United States Patent
Wo et al.

(10) Patent No.: US 7,049,463 B2
(45) Date of Patent: May 23, 2006

(54) PROCESS FOR THE PREPARATION OF HIGHLY PURIFIED, DIALKYL PHOSPHINIC ACIDS

(75) Inventors: Shiming Wo, Monroe Township, NJ (US); Floryan De Campo, Mount Pleasant, SC (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 11/256,704

(22) Filed: Oct. 24, 2005

(65) Prior Publication Data

US 2006/0089508 A1   Apr. 27, 2006

Related U.S. Application Data

(60) Provisional application No. 60/621,972, filed on Oct. 25, 2004.

(51) Int. Cl.
*C07F 9/22* (2006.01)

(52) U.S. Cl. .......................................... 562/8

(58) Field of Classification Search ..................... 562/8
See application file for complete search history.

(56) References Cited

U.S. PATENT DOCUMENTS 6,420,598 B1 *   7/2002   Weferling et al. ............. 562/8

* cited by examiner

*Primary Examiner*—Peter O'Sullivan

(57) ABSTRACT

In a process for the production of dialkylphosphinic acids, especially branched, dialkylphosphinic acids in high purity via the reaction of an alpha olefin with a hypophosphorous acid or a salt thereof, the improvement comprising conducting the reaction in the presence of a stoichiometric excess of the olefin and isolating and purifying the desired dialkylphosphinic acid product by neutralizing the monoalkylphosphinic acid by-product with an aqueous base; removing the aqueous phase in which the neutralized monoalkylphosphinic acid is preferentially solubilized; acidifying the dialkyl product in the organic phase; and isolating the purified product.

17 Claims, No Drawings

PROCESS FOR THE PREPARATION OF HIGHLY PURIFIED, DIALKYL PHOSPHINIC ACIDS

This patent application claims priority from provisional patent application Ser. No. 60/621,972 filed Oct. 25, 2004.

FIELD OF THE INVENTION

The present invention generally relates to an improved process for the economical production of dialkylphosphinic acid compounds, preferably branched dialkylphosphinic acid compounds. The process enables a single phase separation which realizes a high purity dialkylphosphinic acid product.

BACKGROUND OF THE INVENTION

Numerous derivatives of organic phosphinic acids are known to exist and to have considerable commercial value as well as a great variety of useful applications. For example, organic phosphinates as well as their acids are effective wetting agents and detergents; plasticizers for many plastics and resins; bonding agents for asphalt and similar compositions; color stabilizers and oxidation inhibitors for greases and lubricants (U.S. Pat. No. 3,001,938); corrosion inhibitors; flame proofing agents; flotation auxiliaries; metal extractants; setting retarders for gypsum; and textile auxiliaries such as filament stabilizers (U.S. Pat. No. 3,374,288).

Highly purified, highly branched dialkylphosphinic acids have been especially recognized as being very important and much desired precursors, intermediate products, and end products in numerous specialized fields. For example, branched dialkylphosphinic acids act as complex-forming agents; pharmaceutically active materials, especially those suitable for the treatment of inflammations, and degenerative diseases of the joints, such as rheumatoid arthritis (U.S. Pat. No. 4,524,211); general agricultural and household chemicals including plant growth regulators, insecticides, and herbicides; and antistatic agents. In many, if not all of these applications, the presence of monoalkylphosphinic acid by-product can be detrimental due to the reactivity of the phosphorus-hydrogen moiety and the thermal instability of such compounds.

As a result of the above listed numerous possibilities of practical application, a demand has been created for a simple industrial synthesis for the production of these dialkylphosphinic acids in a highly purified state. Because of the aforedescribed great commercial value, many methods of preparing organic phosphinic acids and their phosphinates have been advanced. Although the methods vary widely in their individual steps, a great many employ the reactions of phosphorous-halogen compounds to attain carbon-to-phosphorous bonds. While it has long been known to be possible to form such bonds by reacting alkyl halides with phosphine, or by the use of Grignard reagents, such methods are not practical in commercial scale operations.

Stiles et al. (U.S. Pat. No. 2,724,718) discloses a process for the production of phosphinates employing the reaction between a compound containing olefinic double bonds and, preferably, a class of compounds consisting of compounds of the formula (I):

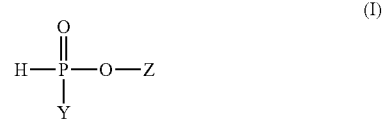

wherein Z represents a monovalent hydrocarbon radical free of aliphatic multiple bonds, or a monovalent inorganic cation, and Y represents a hydrogen atom, a monovalent hydrocarbon radical free of aliphatic multiple bonds, or the group-OZ in which Z is defined as above. Among the phosphorous classes and compounds that Stiles et al. suggest as reactants are the salts of hypophosphorous acid, hydrocarbyl esters of hypophosphorous acid, hydrocarbyl esters of organic phosphinic acids and mono- and di-hydrocarbyl esters of phosphorous acid. A particularly preferred subclass comprises the alkali metal salts of hypophosphorous acid such as sodium hypophosphite which Stiles et al. found to be able to be directly added to olefins containing up to 14 carbon atoms "to produce in a single, operational step a water soluble detergent in substantially quantitative yields."

Stiles et al. also noted that 1-olefins exhibit a somewhat higher rate of reaction in these processes than do other olefins. The Stiles et al. addition reaction is initiated by the presence of free radicals in intimate contact with the reactants. Neither the reaction temperature nor the reaction pressure is taught to be critical by Stiles et al.

Stiles et al. teach that where a mole to mole addition is desired, it is generally preferable to employ the reactants in about equimolar proportions or with the phosphorous compound in excess; and, where it is desirable to cause more than one mole of the olefinic compound to be incorporated in the product, for example to produce a di-alkylphosphinic acid, it is preferable to employ about a 2 to 3 to 1 molar excess of the olefinic compound.

A. J. Robertson (U.S. Pat. No. 4,374,780) discloses the production of a highly branched, dialkyl phosphinic acid namely di-2,4,4'-trimethylpentyl phosphinic acid by the free radical addition of two moles of an alkene, specifically 2,4,4'-trimethylpentene-1, to phosphine gas followed by an oxidation of the phosphine reaction product to the phosphinic acid using two moles of hydrogen peroxide. It is disclosed, however, that high phosphine pressures, i.e., up to about 1000 psig may be necessary to achieve high phosphine to olefin ratios and thus reduce unwanted tri-2,4,4'-trimethylpentylphosphine by-product; for any such by-product formed is a total yield loss. Also, the exothermic oxidation stage is said to be temperature critical for if the temperature exceeds about 120° C., an alkyl group is removed and additional monoalkylphosphinic acid is formed; temperatures below about 50° C., result in excessive reaction times. A straight forward distillation was said to be able to achieve good dialkylphosphinic acid yields.

Of course, monoalkyl- and dialkylphosphinic acids could also be formed by hydrolytic cleavage of the respective alkyl esters, whose phosphorous-carbon bonds had been formed in the first place by other means, at temperatures of from about 160° C. to 300° C. using at least a quantity of water which is required by stoichiometry for the hydrolysis. The alkanol formed as one of the hydrolysis products is usually removed from the reaction mixture by distillation. (U.S. Pat. No. 4,069,247).

Alkyl phosphinic acids have also been used to extract rare earth elements (U.S. Pat. No. 5,639,433). In the general procedure employed for the separation of rare earth elements from solutions thereof, especially acidic solutions, the feed solution generally results from the treatment of ores containing rare earth elements such as monazite, bastnaesite, xenotime, bauxite, and similar crude ores. The extract containing the extracted rare earth element(s) is usually sent to a scrubber wherein it is scrubbed with dilute acid and then sent to a stopper where it is stripped with more concentrated acid to separate the rare earth elements. Hydrochloric acid is the preferred acid of the prior art to scrub and strip the extract. Bis-(2,4,4-trimethylpentyl)phosphinic acid is said to be a preferred extractant; especially for the separation of cobalt from nickel.

Further, with respect to end uses of the dialkylphosphinic acids and their esters, U.S. Pat. No. 6,165,427 discloses the use of a composition comprising sodium di-(n-octyl)phosphinate and sodium di-(n-dodecyl)phosphinate to precipitate and recover soluble heavy metals such as lead, cadmium, zinc species and mixtures thereof from wastewater streams. It is taught that advantageously, the organophosphorus salts may be regenerated from the precipitate by treating the precipitate with concentrated aqueous hydroxide to dissolve it and then contacting the resulting solution with diethyl ether in, for example, a separation funnel. After agitation and subsequent phase disengagement, two phases are present. One phase is an aqueous phase containing the metal with a concentration higher than that of the feed. The other phase is the ether solution of the precipitating agent. The ether is evaporated and the sodium di-(alkyl)phosphinate is regenerated.

Purifications of the alkyl phosphinic acids and their esters are often accomplished via additions of an organic material such as diisopropyl ether or petroleum ether (U.S. Pat. No. 4,434,108); followed by repeated evaporations, crystallizations, and filtrations (U.S. Pat. No. 4,524,211).

The major problem inherent in the aforedescribed processes of the prior art, is that it is extremely difficult to separate the di-alkylphosphinic acids from co-formed mono-alkyl reaction products since they have very similar aqueous solubilities. This art-recognized problem of producing high purity dialkyl phosphinic acids by a practical reaction process which is applicable to the production of compounds having a variety of structures, especially highly branched dialkyl structures, has heretofore remained unsolved.

Accordingly, it is an object of this invention to provide a practical and efficient process for addressing this technical problem by providing conditions whereby, in a straightforward alpha olefin-hypophosphorous acid or a salt thereof free radical reaction, any monoalkylphosphinic acid and other water soluble impurities present are removed from the di-alkylphosphinic acid product by a simple neutralization/ phase separation without the need for a third component organic solvent addition.

Other objects will be evident from the ensuing description and appended claims.

SUMMARY OF THE INVENTION

The present invention relates to a process wherein a straightforward synthesis of dialkylphosphinic acids, especially branched dialkylphosphinic acids and their phosphinates can be produced with high purity using standard reaction processing and apparatus, i.e., in the absence of high pressures and temperatures; and straightforward aqueous phase extraction/separation processing without the need for an additional organic solvent addition step and the attendant recovery procedures and equipment for the necessary additional solvent recovery.

The improved process permits the production of dialkyl phosphinic acids in high purity by the free radical reaction of an alpha olefin with certain phosphorus compounds wherein the olefin is used in excess in order to provide the solvent medium for the reaction product and subsequently isolating the dialkylphosphinic acid by preferentially neutralizing any monoalkylphosphinic acid by-product; extracting same with an aqueous wash; and isolating and purifying the desired dialkyl phosphinic acid from the excess olefin reactant solvent by art recognized techniques such as acidification, filtration, and distillation.

This is accomplished firstly by the use of excess alpha olefin which subsequently functions as the preferential solubility medium phase for the dialkylphosphinic acid; and secondly, by the recognition that by creating a basic pH environment, the alkali or alkali earth ester of the monoalkylphosphinic acid is significantly more soluble in the aqueous phase than in the organic phase, i.e., the excess olefin reactant phase, than the dialkylphosphinic acid ester product.

DETAILED DESCRIPTION OF THE INVENTION

The subject of the present invention is an improved process for the preparation of purified dialkylphosphinic acids, preferably dialkylphosphinic acids of the formula (I):

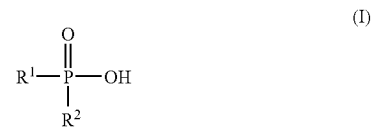

wherein $R^1$ and $R^2$ are each independently, i.e., either identical or different, an alkyl radical having from 2 to 22 carbon atoms, these radicals optionally substituted, preferably di- or higher substituted by chloro, bromo, alkyl or alkoxy groups or mixtures thereof, each alkyl or alkoxy group individually having from 1 to 4 carbon atoms; by the free radical enhanced reaction of hypophosphorous acid or its salts with a stoichiometric excess of an alpha olefin and isolating and purifying the dialkylphosphinic acid reaction product by adding an aqueous base solution which has been found to preferentially neutralize any monoalkylphosphinic acid by-product formed by the reaction. The monoalkyl phosphinic acid, being more soluble in the aqueous phase than in the organic phase where the dialkylphosphinic acid is preferentially solubilized, is easily separated from the dialkylphosphinic acid product. Optionally, for higher purification of the dialkylphosphinic acid, additional purification steps well known by those skilled in the art may be used, such as a subsequent acidification and distillation.

In this manner, unwanted impurities, such as unreacted alkenes, water, or other volatiles can be easily removed from the dialkyl product.

Preferably $R^1$ and $R^2$ are identical.

The alpha olefins used in the process of the invention contain from 2 to 22 carbon atoms, preferably from 2 to 12 carbon atoms and most preferably from 2 to 9 carbon atoms. In the process of the invention, although straight-chain alpha mono-olefins can be used, preferably the alpha mono olefins are branched, most preferably highly branched. Examples of such olefins are: ethylene, propene, butene-(1), hexane-(1), octane-(1), dodecene-(1), tetradecene-(1), hexadecene-(1), octadecene-(1), heneicosene-(1), docosene-(1), 2-methylpentene-(1), 2-ethylhexene-(1), and diisobutylene-(1). Also mixtures of such olefins may be used.

The alpha-olefins which are used as starting compounds in the instant process are obtained by processes well known in the art including the cracking of petroleum distillates or waxes, by splitting off hydrochloric acid from paraffins with terminal chlorine atoms, or by dehydration of alcohols with a terminal hydroxyl group.

The reaction initiator/generator compound may be any compound that readily dissociates either under the influence of temperature, preferably between about 24° C. and 200° C. and/or actinic light. As free radical forming agents in the process of the invention, all known radical forming substances may be used, for example: positive halogen compounds such as calcium hypochlorite, sodium N-chloro-p-toluenesulfonamide, and sodium N-chlorobenzenesulfonamide; metallo-alkyl compounds such as lead tetraethyl and lead tetraphenyl; carbonyl compounds such as acetone, methyl ethyl ketone, and benzaldehyde; and the organic peroxides such as di-tertiary-butyl peroxide, tertiary-butyl hydroperoxide, di-cumylperoxide, benzoylperoxide; tertiary-butyl perbenzoate, 2,5-dimethyl-bis-2,5-(peroxybenzoate), 2,2-bis(tertiary-butylperoxy)butane and benzoyl peroxide. Advantageously, di-tert-butylperoxide is used.

The radical forming agent(s) is used in catalytically effective amounts and may be varied over wide limits depending on the character of the particular initiator. In general, usually from about 0.5 mole percent to about 10 mole percent of reaction initiator, based on the phosphorus reactant, is suitable.

In order to solubilize the free radical generator in the reaction mixture, it may be necessary to add an inert solvent as a dissolving agent. It is preferable, however, that the free radical generator be selected so that it is able to be dissolved in at least one of the reactants; i.e., the alpha olefin or the hypophosphorous acid or a salt thereof. All of the free radical generator-reactant composition can be added at the beginning of the reaction or added subsequently in portions into the reaction vessel.

In the situation wherein the reaction is started by ultraviolet radiation, the reaction solution has to be exposed to direct radiation by an ultraviolet lamp.

It may be advantageous to add any suitable transition metal catalyst to further improve the reaction rate. Suitable transition metal catalyst include, but are not limited too, salts of nickel, cobalt, iron and chromium.

The reaction according to the invention is advantageously carried out as follows: The alpha olefin, optionally mixed with catalytic amounts of a radical forming agent, is slowly introduced into hypophosphorous acid or a salt thereof.

The reaction of the instant invention should occur in the presence of an excess of the alpha olefin, i.e., the ratio of the olefin to the hypophosphorous acid or its salt should be greater than 2 to 1; preferably greater than 2.5 to 1.

The presence of acid has been found to have a positive effect on the yield of the dialkylphosphinic acids in olefin phosphination reactions. It has been theorized that the acid catalyzes the breakdown of the organic peroxide initiator favoring the formation of the dialkylphosphinic acid and also that the acid converts the phosphorous salt to its acid form. Therefore, preferably the reaction takes place in the presence of a yield enhancingly effective amount of an acid(s). Suitable acids are inorganic as well as organic acids insofar as they do not decompose or cause negative side reactions under the primary reaction conditions. Suitable examples are hydrochloric acid, sulfuric acid, and/or, most preferably, acetic acid.

The reaction may also be carried out in the presence of inert solvents, for example alcohols, esters, or hydrocarbons, such as benzene. However, it is much preferred to conduct the reaction in the absence of an additional solvent component.

When the initial reaction is completed, water may be added to adjust the viscosity of the product composition for ease in subsequent processing.

To enhance separation and purification of the dialkylphosphinic acid from the monoalkylphosphinic acid by-product and other undesirable impurities, the organic phase is intimately washed with a basic solution, preferably caustic, which preferentially neutralizes the monoalkylphosphinic acid. The resulting aqueous layer, in which the monoalkylphosphinic acid is highly soluble, is removed. The dialkylphosphinic acid product can be isolated from the reaction mixture and purified by well-known, art recognized techniques such as fractional distillation, the wipe film evaporation, and/or conventional washing techniques. Preferably, to further purify the desired dialkylphosphinic acid product, which is solubilized in the organic medium phase, primarily the alpha olefin reactant which was originally added to the reaction vessel in excess, the organic phase is acid washed, preferably with an inorganic acid such as sulfuric acid. The aqueous phase is again removed and the organic phase filtered and distilled to remove any final impurities and volatile materials.

Examples of specific compounds that may be prepared include: di-(2,4,4-trimethylpentyl)phosphinic acid, and di-(2-ethylhexyl)phosphinic acid.

The temperature employed in the process of this invention can be varied depending on factors known to those skilled in the art. Reaction will generally be carried out at temperatures within the range of from about 24° C. to about 200° C. and reaction temperatures of from about 100° C. to about 150° C. are particularly preferred. In the most preferred embodiments of the invention, the reaction is conducted at a temperature of from about 110° C. to about 140° C.

The reaction may be carried out at atmospheric pressure or above atmospheric pressure in a sealed vessel.

The process of this invention is conducted for a period of time sufficient to produce the desired compound in adequate yield. Reaction times are influenced to a significant degree by the reaction temperature; the concentration and choice of reactants; and other factors known to those skilled in the art. In general, reaction times can vary from 8 hours to several days or longer.

If the alpha olefin is initially used in its pure form, the excess alpha olefin can be recycled.

The process of this invention is preferably conducted in a batch or semi-continuous fashion. The reaction can be conducted in a single reaction zone or in a plurality of reaction zones or it may be conducted intermittently in an elongated tubular zone or series of such zones. The materials of construction employed should be inert to the reactants during the reaction and the equipment should be fabricated such that it is able to withstand the reaction temperatures and pressures.

The invention will now be described with reference to a specific example which is to be regarded solely as illustrative of the methods and compositions of this invention and not as restrictive of the scope thereof.

EXAMPLE I

Synthesis

To synthesize bis(2,4,4-trimethylpentyl)phosphinic acid, a 1.5 liter autoclave was charged with 40 g (0.377 moles) of sodium hypophosphite; 40 g of acetic acid; 132.3 g (0.943 moles) of diisobutylene (80%); and 2.8 g (0.019 moles) of tert-butyl peroxide initiator. The mixture was then heated to about 135° C. during an 8 hour day for about four days, i.e., a total of 30 hours and 1.4 g of the initiator was added at the beginning of each day. The reaction mixture was monitored by $^{31}$P NMR and resulted in the composition identified in Table I below. The original mixture contained 75.3% of the desired dialkylphosphinic acid product and 12.1% of the undesired monoalkylphosphinic acid by-product.

Purification

The completed reaction mixture (220 g) was transferred to an Erlenmeyer flask and heated in the range of from about 70° C. to about 80° C. to reduce the viscosity. 38 g of water was slowly added until two phases were observed. The aqueous phase was removed and its pH was measured to be about 5. The organic phase was then washed with 75 g of a 4% caustic solution and the resulting aqueous layer (89.2 g) was removed. The organic layer was acidified and washed with 50 g of a 10% sulfuric acid solution and the resulting aqueous phase removed.

The acidified and washed organic phase was filtered through PS paper and volatile materials were removed by vacuum distillation. 95 g of dialkylphosphinic acid product were recovered with a purity of 93.7% based on phosphorous NMR; thus a yield of 86.9%. The composition of the final product is identified in Table I below.

TABLE I

| Components | Initial Reaction Product Mixture (%) | Reaction Product Mixture After Purification (%) |
| --- | --- | --- |
| Unreacted Hypophosphorus Acid | 1.6 | 0 |
| Monoalkylphosphinic Acid | 12.1 | 0 |
| Dialkylphosphinic Acid | 75.3 | 93.7 |
| Other Impurities | 11.0 | 6.3 |

From the above Example and the detailed descriptions of the process in the body of this specification, it can be readily seen that the process of this invention permits the preparation of dialkylphosphinic acids, especially branched dialkylphosphinic acids of high purity in a simple manner with very good yields and therefore represents a significant advance in the industrial art.

Although this invention has been described in detail with particular reference to preferred embodiments thereof, it will be understood that variations and modifications can be effected within the spirit and scope of this invention as described hereinabove and as defined in the appended claims.

We claim:

1. An improved process for the production of dialkylphosphinic acid in high yield and purity by the reaction of a hypophosphorous acid or salt with a stoichiometric excess of an alpha olefin in the presence of a free radical initiator and optionally a transition metal catalyst to form a reaction product composition comprising monoalkylphosphinic acid and dialkylphosphinic acid; the improvement comprising:

a) adding sufficient aqueous base to the reaction product composition to i) form the salts of the phosphinic acids, and ii) establish an aqueous phase and an organic phase, wherein the monoalkylphosphinic acid preferentially solubilizes into the aqueous phase;

b) separating the organic phase from the aqueous phase;

c) acidifying the organic phase; and d) removing the olefin from the organic phase; and e) isolating the purified dialkylphosphinic acid product.

2. The process of claim 1 wherein the dialkylphosphinic acid is of the following formula:

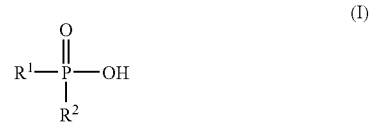

wherein $R^1$ and $R^2$ are each independently an alkyl radical having from 2 to 22 carbon atoms.

3. The process of claim 2 wherein $R^1$ and $R^2$ are each independently a substituted alkyl radical having from 2 to 12 carbon atoms.

4. The process of claim 3 wherein the $R^1$ and $R^2$ are each independently a substituted alkyl radical having from 2 to 9 carbon atoms.

5. The process of claim 2 wherein the alkyl radicals are each independently substituted by two or more radicals selected from the group consisting of chloro-, bromo, alkyl, alkoxy groups and mixtures thereof.

6. The process of claim 3 wherein the alkyl radicals are each independently substituted by two or more radicals selected from the group consisting of chloro-, bromo, alkyl, alkoxy groups and mixtures thereof.

7. The process of claim 4 wherein the alkyl radicals are each independently substituted by two or more radicals selected from the group consisting of chloro-, bromo, alkyl, alkoxy groups and mixtures thereof.

8. The process of claim 1 wherein the reaction to form the reaction product composition takes place in the presence of an acid solution.

9. The process of claim 8 wherein the acid solution is selected from the group consisting of hydrochloric acid, sulfuric acid, acetic acid and mixtures thereof.

10. The process of claim 9 wherein the acid solution is an acetic acid solution.

11. The process of claim 1 wherein the hypophosphorous salt is sodium hypophosphite monohydrate.

12. The process of claim 1 wherein the molar ratio of the alpha olefin to the hypophosphorous acid or salt is greater than 2:1.

13. The process of claim 12 wherein the molar ratio of the alpha olefin to the hypophosphorous acid or salt is greater than 2.5 to 1.

14. The process of claim 1 wherein the aqueous base which is added to the reaction product composition is an aqueous sodium hydroxide solution or an aqueous sodium carbonate solution.

15. The process of claim 1 wherein the acid in the acidification step comprises an inorganic acid solution.

16. The process of claim 15 wherein the inorganic acid solution is a sulfuric acid solution.

17. The process of claim 1 wherein the olefin removed is recycled.

* * * * *